United States Patent [19]

Bélanger et al.

[11] Patent Number: 4,720,505
[45] Date of Patent: Jan. 19, 1988

[54] LEUKOTRIENE ANTAGONISTS

[75] Inventors: Patrice C. Bélanger; John W. Gillard, both of Quebec; Joshua Rokach, Laval, all of Canada

[73] Assignee: Merck Frosst Canada, Inc., Kirkland, Canada

[21] Appl. No.: 670,784

[22] Filed: Nov. 13, 1984

Related U.S. Application Data

[63] Continuation-in-part of Ser. No. 508,318, Jun. 27, 1983, abandoned.

[51] Int. Cl.$^4$ ............... C07C 149/40; C07C 147/107; C07C 143/67; C07C 101/00; C07C 151/00; C07C 147/11; C07C 147/13; C07C 101/72

[52] U.S. Cl. .................................. 514/532; 514/534; 514/535; 514/544; 514/557; 514/561; 514/562; 514/568; 514/570; 560/9; 560/11; 560/12; 560/19; 560/45; 560/46; 560/55; 560/64; 560/65; 562/426; 562/429; 562/430; 562/432; 562/442; 562/452; 562/453; 562/465; 562/473; 562/474

[58] Field of Search ............... 562/426, 429, 430, 432, 562/442, 452, 453, 465, 473, 474; 560/9, 11, 12, 19, 45, 46, 55, 64, 65; 514/532, 534, 535, 544, 557, 561, 562, 568, 570

[56] References Cited

U.S. PATENT DOCUMENTS 4,667,055 5/1987 Gillard et al. ..................... 562/426

FOREIGN PATENT DOCUMENTS 56172  7/1982 European Pat. Off. .
61800 10/1982 European Pat. Off. .
68739  1/1983 European Pat. Off. .
0048404 4/1984 European Pat. Off. .
1204122 9/1970 United Kingdom .
2058785 4/1981 United Kingdom .

OTHER PUBLICATIONS

D. M. Bailey et al., Ann Rpts. Med. Chem, 17, 203 (1982).
B. Samuelsson, Science 220, 568 (1983).

Primary Examiner—Alan Siegel
Attorney, Agent, or Firm—Gabriel Lopez; Hesna J. Pfeiffer; Paul H. Ginsburg

[57] ABSTRACT

Compounds having the formula:

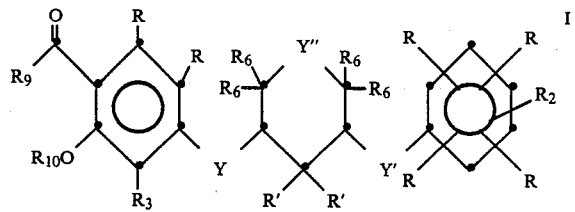

are antagonists of leukotrienes of $C_4$, $D_4$ and $E_4$, the slow reacting substance of anaphylaxis. These compounds are useful as anti-asthmatic, anti-allergic and anti-inflammatory agents.

4 Claims, No Drawings

LEUKOTRIENE ANTAGONISTS

CROSS REFERENCE TO RELATED APPLICATION

This application is a continuation-in-part of U.S. Ser. No. 508,318, filed June 27, 1983, now abandoned.

BACKGROUND OF THE INVENTION

Although the chemical identity of leukotrienes was not discovered until 1979, their history actually began in Australia in 1938 when researchers discovered slow reacting substances (SRS) which caused slow contractions of smooth muscle. When their chemical identity was learned, SRS was found to be a mixture of three previously unknown substances which are related chemically to the prostaglandins and thromboxanes. They were named leukotrienes because they are made by leukocytes and have three conjugated double bonds. Leukotrienes have major effects on the smaller peripheral airways of the lungs and on the larger central passages which include the trachea and the bronchi. In the presence of an allergy trigger, like pollen or dust, leukotrienes are manufactured from fatty substances trapped in the membrane of a triggered cell. A series of reactions within the cell generates a set of different leukotrienes which are transported through the cell membrane into the blood. Then they bring about a constriction of the air passages leading to breathlessness. In addition, the leukotrienes have been implicated in a number of additional disease states; such as, inflammation, allergic reactions, skin diseases and cardiovascular problems, among others. See for example, D. M. Bailey et al., *Ann. Repts. Med. Chem.*, 17 203 (1982), and B. Samuelsson, *Science*, 220 568 (1983).

Several classes of compounds exhibit ability to antagonize the action of leukotrienes in mammals, especially humans. See for example: Great Britain Patent Specification No. 2,058,785; and European Patent Application Nos. 56,172 and 61,800.

OBJECTS OF THE INVENTION

It is an object of the present invention to provide compounds that act as antagonists to prevent leukotriene action or as inhibitors to prevent synthesis. A further object is to provide compounds which prevent or reverse leukotriene action or prevent leukotriene synthesis when administered orally. Yet another object is to provide compounds which prevent or reverse leukotriene action or prevent leukotriene synthesis when administered by insufflation, intravenously, rectally, topically, parenterally including subcutaneously and intramuscularly, or nasally. Another object is to provide methods for the preparation of these compounds. A further object is to provide intermediates useful in the synthesis of these compounds. Still another object is to provide pharmaceutical formulations for administering these compounds. These and other objects of the present invention will be apparent from the following description.

DETAILED DESCRIPTION

The present invention relates to compounds having activity as leukotriene antagonists, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic exzema. These compounds are also useful to antagonize or inhibit the pathologic actions of leukotrienes on the cardiovascular and vascular systems.

The compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of the present invention have the formula I:

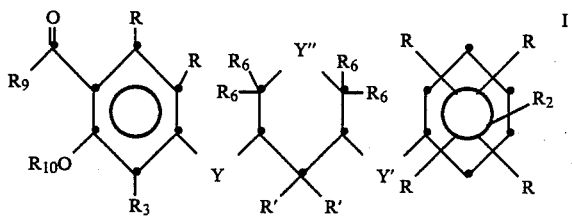

wherein each R is independently H; OH; alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$; phenyl; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are $=O$; $CH_2$; or

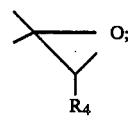

Y is oxygen; sulfur; sulfoxide; sulfone;

wherein $R_{11}$ is alkyl of 1–4 carbon atoms which may be straight chain or branched; $NR_{12}$ wherein $R_{12}$ is H, alkyl of 1 to 4 carbon atoms which may be straight chain or branched; or

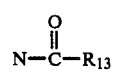

wherein $R_{13}$ is alkyl of 1 to 4 carbon atoms which may be straight chain or branched, alkoxy of 1 to 4 carbon atoms which may be straight chain or branched; N—CN; or NCONHR$_{12}$;

Y'' and Y' are each independently Y, —CH$_2$— or $$\overset{O}{\underset{}{=\!\!C\!\!-}};$$

R$_2$ is $$-\overset{\overset{Z}{\|}}{(C)_p}-\overset{\overset{R_6}{|}}{\underset{\underset{R_7}{|}}{(C)_r}}-\left[\overset{\overset{R_8}{|}}{\underset{\underset{R_8}{|}}{C\!\equiv\!C}}\right]_p-\overset{\overset{R_6}{|}}{\underset{\underset{R_7}{|}}{(C)_q}}-R_5$$

wherein Z is O; S; CH$_2$; alkenyl of 1 to 4 carbons; or N—R$_{14}$ wherein R$_{14}$ is OH, N(R$_4$)$_2$, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;

each R$_4$ is independently H or alkyl of 1 to 6 carbon atoms which may be straight chain or branched;

each R$_6$ is independently H or alkyl of 1 to 4 carbons;

each R$_7$ is independently H, OH, or alkyl of 1 to 4 carbons;

each R$_8$ is independently H, or alkyl of 1 to 4 carbons, and is absent when a triple bond is present;

R$_5$ COOR$_4$; CH$_2$OH; CHO; tetrazole; NHSO$_2$R$_{14}$; hydroxymethylketone; CN; CON(R$_7$)$_2$; a monocyclic or bicyclic heterocyclic ring containing an acidic hydroxyl group; or $$-COO(CH_2)_s-\overset{\overset{R_6}{|}}{\underset{\underset{R_6}{|}}{C}}(CH_2)_s-R_{15}$$

wherein each s is independently 0 to 3; R$_{15}$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical X—R$_{16}$ wherein X is O, S or NH and R$_{16}$ contains up to 21 carbon atoms and is (1) a hydrocarbon radical or (2) an acyl radical of an organic acyclic or monocyclic carboxylic acid containing not more than 1 heteroatom in the ring;

r and q are each independently 0 to 20 provided that the total of r and q does not exceed 20; and p is 0 or 1;

R$_3$ is alkyl of 1 to 6 carbon atoms which may be straight chain or branched; or alkenyl of 3 to 6 carbon atoms which may be straight chain or branched;

R$_9$ is alkyl of 1 to 6 carbon atoms which may be straight chain or branched; alkoxy of 1 to 6 carbon atoms which may be straight chain or branched; or (CH$_2$)$_r$R$_5$;

R$_{10}$ is H; alkyl of 1 to 6 carbon atoms which may be straight chain or branched;

$$\underset{R_4C-}{\overset{O}{\|}}$$

or R$_4$OCH$_2$—;

and a pharmaceutically acceptable salt or acid addition salt thereof.

A preferred embodiment of the present invention are compounds of Formula I wherein each R is independently H; alkyl of 1 to 6 carbon atoms which may be straight chain or branched; trifluoromethyl; alkoxy of 1 to 6 carbon atoms which may be straight chain or branched; thioalkyl of 1 to 6 carbon atoms which may be straight chain or branched; halogen; N(R$_4$)$_2$; formyl; CN; or trifluoromethylthio;

each R' is independently R$_4$; OR$_4$; or together R' and R' are =O;

Y is oxygen; sulfur; sulfoxide; sulfone; or N—CN;

Y'' and Y' are independently Y or —CH$_2$—;

R$_2$ is $$-\overset{\overset{Z}{\|}}{(C)_p}-\overset{\overset{R_6}{|}}{\underset{\underset{R_7}{|}}{(C)_r}}-\overset{\overset{R_6}{|}}{\underset{\underset{R_7}{|}}{(C)_q}}-R_5$$

wherein Z is O, S, or N—R$_{14}$ wherein R$_{14}$ is OH, N(R$_4$)$_2$, alkyl or alkoxy of 1 to 6 carbon atoms;

each R$_4$ is independently H or alkyl of 1 to 6 carbon atoms which may be straight chain or branched;

each R$_6$ is independently H or alkyl of 1 to 4 carbons;

each R$_7$ is independently H, OH, or alkyl of 1 to 4 carbons;

R$_5$ is COOR$_4$; CH$_2$OH; CHO; tetrazole; NHSO$_2$R$_{14}$; hydroxymethylketone; CN; CON(R$_7$)$_2$; or a monocyclic or bicyclic heterocyclic ring containing an acidic hydroxyl group;

r and q are each independently 0 to 5; and p is 0 or 1;

R$_3$ is alkyl of 1 to 6 carbon atoms which may be straight chain or branched; or alkenyl of 3 to 6 carbon atoms which may be straight chain or branched;

R$_9$ is alkyl of 1 to 6 carbon atoms which may be straight chain or branched;

R$_{10}$ is H; alkyl of 1 to 6 carbon atoms which may be straight chain or branched;

$$\underset{R_4C-}{\overset{O}{\|}}$$

or R$_4$OCH$_2$—;

and a pharmaceutically acceptable salt or acid addition salt thereof.

A more preferred embodiment are compounds of formula IA:

wherein
each R is independently H, alkyl of 1 to 6 carbon atoms which may be straight chain or branched; trifluoromethyl; halogen; or $N(R_4)_2$;
each R' is independently $R_4$ or $OR_4$;
Y' is oxygen, sulfur, sulfoxide or sulfone;
$R_2$ is

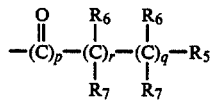

wherein:
each $R_4$ is independently H or alkyl of 1 to 6 carbon atoms which may be straight chain or branched;
each $R_6$ is independently H or alkyl of 1 to 4 carbons;
each $R_7$ is independently H, OH, or alkyl of 1 to 4 carbons;
$R_5$ $COOR_4$;
r and q are each independently 0 to 3; and
p is 0 or 1;
$R_3$ is alkyl of 1 to 6 carbon atoms which may be straight chain or branched; or alkenyl of 3 to 6 carbon atoms which may be straight chain or branched;
$R_9$ is alkyl of 1 to 6 carbon atoms which may be straight chain or branched;
and a pharmaceutically acceptable salt or acid addition salt thereof.

SCHEME I

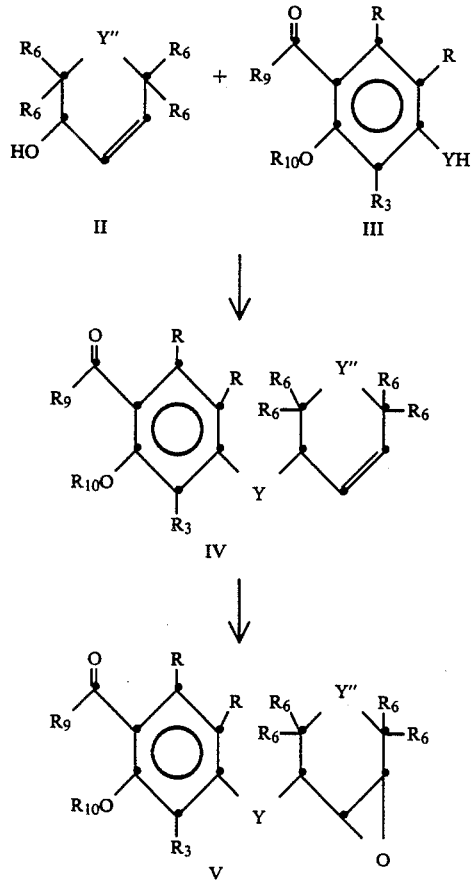

-continued
SCHEME I

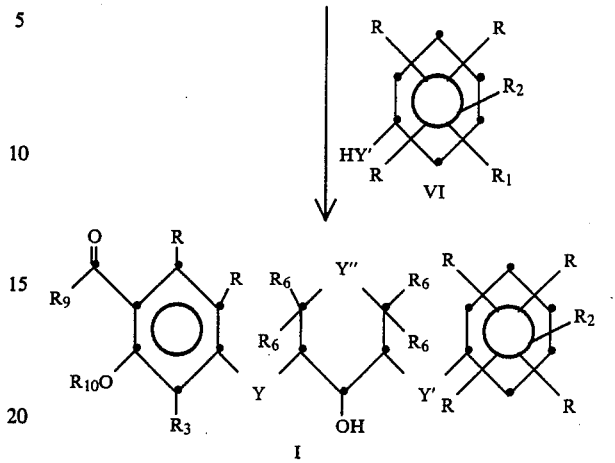

The compounds of the present invention may be prepared by several different routes. According to one method, illustrated in Scheme I, a compound of formula II is reacted with a suitable compound III using diethyl diazodicarboxylate and triphenylphosphine, according to O. Mitsumobo, *Synthesis* 1 (1981), to yield the novel intermediate IV. An alternate procedure to IV involves the displacement of the mesylate or arylsulfonate of II, or its corresponding chloride, bromide, iodide by III in the presence of a base, such as potassium carbonate in a solvent such as methyl ethyl ketone. Other suitable bases could be an alkali metal carbonate such as $Li_2CO_3$, or $Na_2CO_3$. The reaction could also be carried out in other solvents such as THF, glyme, diglyme on DMF. The temperature range to carry out this transformation is 25°–160° C., the optimum being 60°–70° C.

Specific examples of allylic alcohols of formula II are cyclopenten-2-ol, cyclohexen-2-ol, cyclohepten-2-ol, cycloocten-2-ol, and cyclododecen-2-ol, all readily available from the corresponding α,β-unsaturated ketone.

Compound IV is then allowed to react with an organic peracid, such as, for example, m-chloroperbenzoic acid to give the epoxide compound V. The epoxidation is best carried out in an inert solvent, such as $CH_2Cl_2$ but other solvents such as chloroform or dichloroethane can also be used.

The epoxide V is then reacted with a derivative VI under the same conditions used to react the mesylate of a compound of formula II with a compound of formula III to give a compound Ia.

When Y' is methylene or carbonyl a stronger base such as, for example, lithium diisopropylamide or butyl lithium is employed in an inert solvent such as tetrahydrofuran with a suitable compound of formula VI.
When Y' is $-CH_2$, HY' is methyl. When Y' is

HY' is a protected aldehyde, such as, for example, dithioacetal.

A compound of formula VI is prepared by subjecting a compound of the formula X

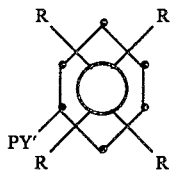

wherein P is H or a protecting group such as, for example, methyl, benzyl, p-nitrobenzyl or 3-(m-nitrophenyl)-1-phenyl-1-oxo-3-propyl, to a Friedel-Crafts reaction with an acyl halide or an acid anhydride.

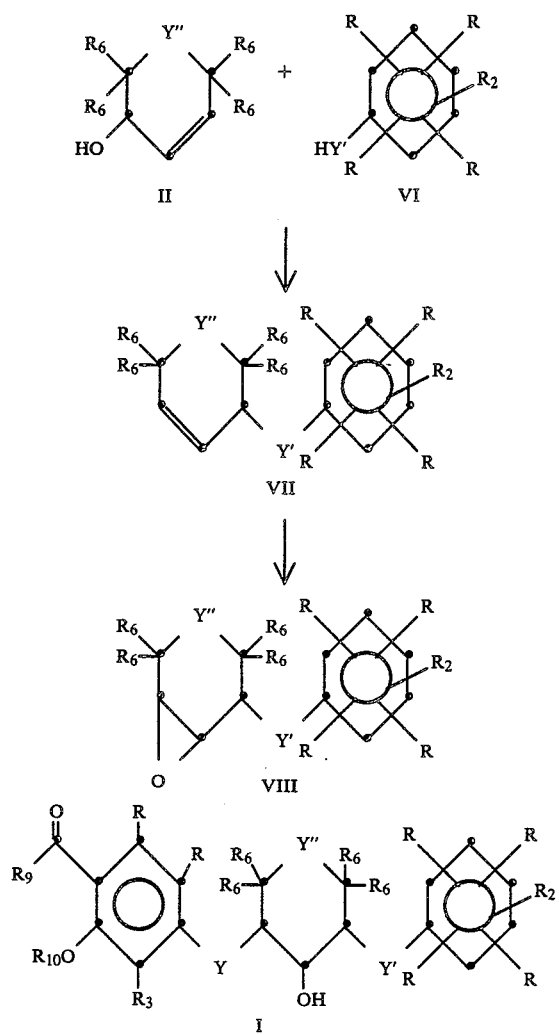

An alternate preparation of I as illustrated in Scheme II involves the reaction of II with VI under the conditions already used successfully for reacting II and III. The intermediate olefin of structure VII is then epoxidized by reacting it with an organic peracid such as m-chlorobenzoic acid to yield an epoxide derivative of structure VIII. It is then easily reacted with a compound of formula III to yield I.

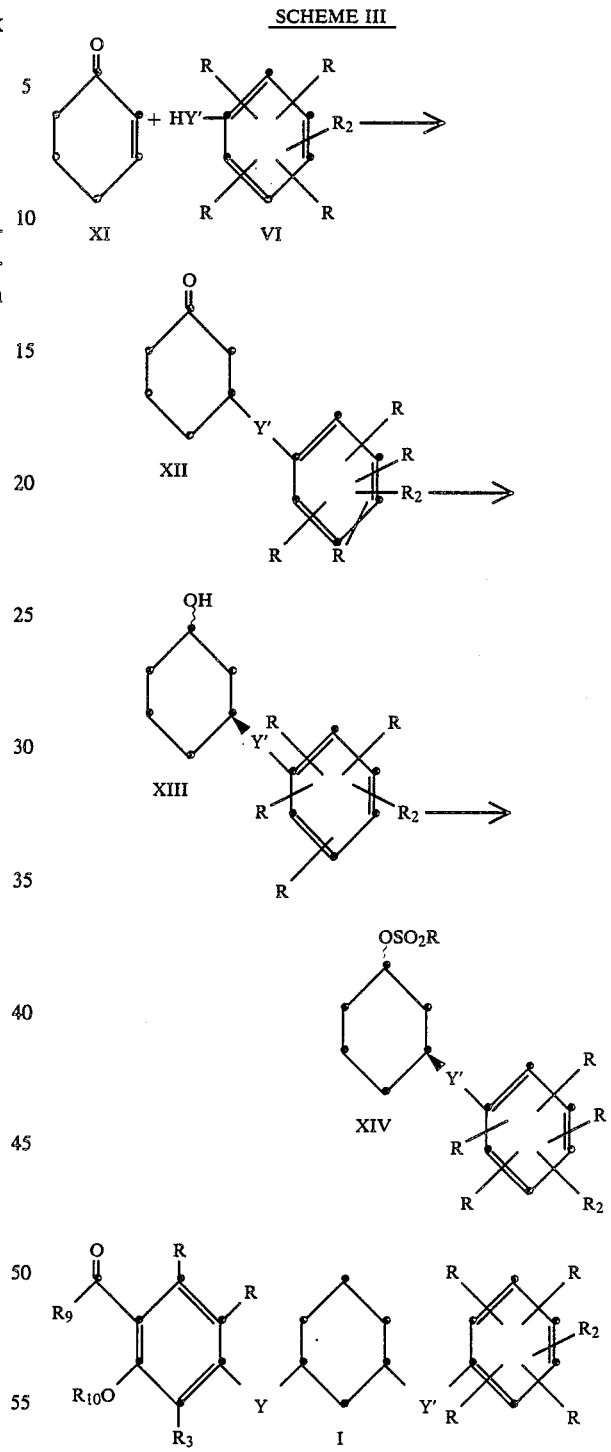

For the preparation of compounds of formula I where $R'=H$, Scheme III is followed. Thus, when the thiol VI is reacted with a cycloalkanone XI in the presence of a base such as tetramethylguanidine, in a protic solvent, the Michael adduct XII is produced. Reduction of the Michael adduct XII with a reducing agent, L-selectride being the preferred reducing agent, a mixture of 2 isomeric alcohols XIII are produced. The trans isomer is the major one formed and it is readily separable by chromatography. Displacement of the mesylate XIV of these alcohols gives rise to the desired final compounds I, where $R_1$ is H.

An alternate preparation of I, as illustrated by Scheme IV, involves the reaction of a mixture of cis and trans cyclohexanediol XV with 1 equivalent of sulfonyl chloride such as methanesulfonylchloride or p-toluenesulfonyl chloride in a inert solvent containing a base such as triethylamine. The mixture of cis and trans mesyl derivative XVI is then reacted with 2.4-dihydroxy-3-propyl acetophenone in an inert solvent using NaH as a base and 15-crown-5. The cis and trans 3-(4-acetyl-3-hydroxy-2-propyl)-cyclohexanol compounds XVII and XVIII are readily separated by chromatography on silica gel. Each of these derivatives, after reaction with sulfonyl chloride in presence of base affords the corresponding sulfonate XIX and XX which in turn can be displaced by a properly substituted hydroxyphenyl derivative to yield compounds XXI and XXII. Base hydrolysis affords compounds of the formula I.

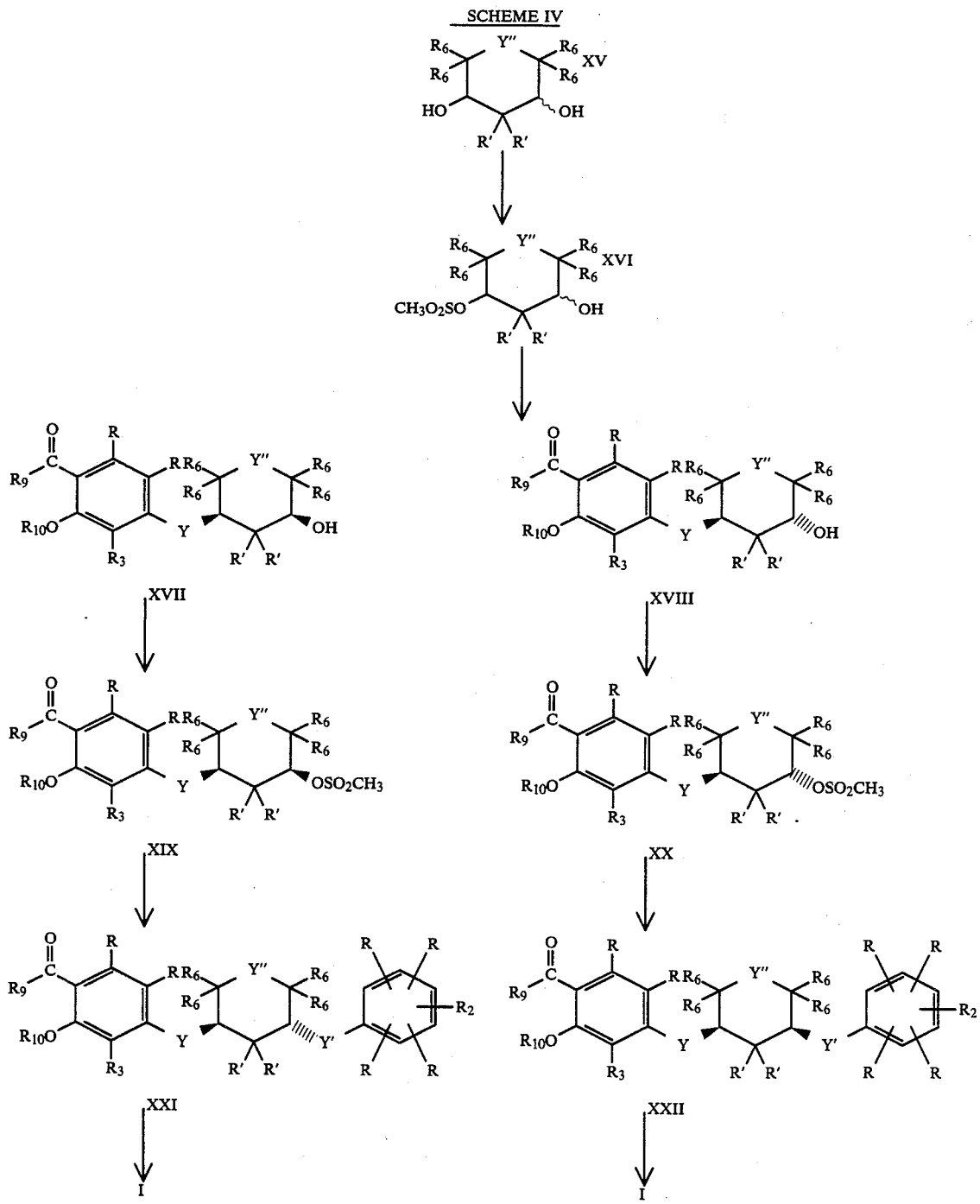

In those instances when assymetric carbon atoms are present, more than one stereoisomer is possible, and all possible isomeric forms are deemed to be included within the planar structural representations shown. Optically active (R) and (S) isomers may be resolved using conventional techniques known to the skilled artisan.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer

Twenty-four fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucoase are examined for resulting ulcers.

The magnitude of a prophylatic or therapeutic dose of a compound of formula I will, of course, vary with the nature of the severity of the condition to be treated and with the particular compound of formula I and its route of administration. In general, the daily dose range for anti-asthmatic, anti-allergic or anti-inflammatory use lies within the range of from about 0.2 mg to about 100 mg per kg body weight of a mammal.

The exact amount of a compound of the Formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent.

The effective daily dosage level for compounds of Formulae I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intraveneous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salt derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intraveneous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intraveneous administration is employed, a suitable dosage range for anti-asthmatic, anti-inflammatory or anti-allergic use is from about 0.01 mg to about 20 mg (preferably from about 0.1 mg to about 10 mg) of a compound of formula I per kg of body weight per day and for cytoprotective use from about 0.002 mg to about 100 mg (preferably from about 0.02 mg to about 30 mg and more preferably from about 0.1 mg to about 10 mg) of a compound of formula I per kg of body weight per day. In the case where an oral composition is employed, a suitable dosage range for anti-asthmatic, anti-inflammatory or anti-allergic use is, e.g. from about 1 to about 100 of a compound of formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to the conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene antagonists of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the leukotriene antagonists of Formula I:

| Injectable Suspension | mg/ml |
| --- | --- |
| Compound of Formula I | 2 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Tablet | mg/tablet |
| --- | --- |
| Compound of Formula I | 25.0 |
| Microcrystalline Cellulose | 415.0 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free $-CH(CH_3)COOH$ or $-CH_2CH_2COOH$ group (which optionally can be in the form of a pharmaceutically acceptable salt group, e.g., $-CH(CH_3)COO^-Na^+$ or $-CH_2CH_2COO^-Na^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and antiinflammatory properties are also intended to the encompassed by this group.

Thus, "acetic acid derivatives" as defined herein are non-narcotic analgesics/non-steroidal antiinflammatory drugs having a free $-CH_2COOH$ group (which optionally can be in the form of a pharmaceutically acceptable salt group, e.g. $-CH_2COO^-Na^+$), typically attached directly to a ring system, preferably to an aromatic or heteroaromatic ring system.

The fenamic acid derivatives which may be used comprise: mefanamic acid, meclofenamic acid, flufenamic acid, niflumic acid and tolfenamic acid. Structurally related fenamic acid derivatives having similar analgesic and anti-inflammatory properties are also intended to be encompasses by this group.

Thus, "fenamic acid derivatives" as defined herein are non-narcotic analgesics/non-steroidal anti-inflammatory drugs which contain the basic structure:

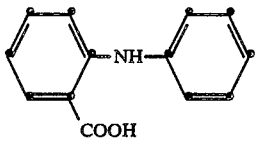

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammtory properties are also intended to be encompassed by this group.

Thus, "biphenylcarboxylic acid derivatives" as defined herein are non-narcotic analgesics/non-steroidal anti-inflammatory drugs which contain the basic structure:

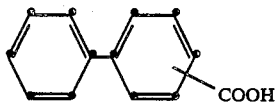

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4-hydroxy-1,2-benzothiazine 1,1-dioxide 4-(N-phenyl)-carboxamide. Structurally related oxixcams having similar analgesic and anti-inflammatory properties are also intended to be encompassed by this group.

Thus, "oxicams" as defined herein are non-narcotic analgesics/non-steroidal anti-inflammatory drugs which have the general formula:

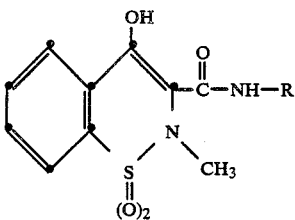

wherein R is an aryl or heteroaryl ring system.

The following NASIDs may also be used: acemetacin, alminoprofen, amfenac sodium, aminoprofen, anitrazafen, antrafenine, auranofin, bendazac lysinate, benzyldamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodalac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepec, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITC1, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent applications Ser. No. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European patent application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European patent application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an H$_1$ or H$_2$-receptor antagonist, such as for instance cimetidine, ranitidine, terfenadine, famotidine, aminothiadiazoles disclosed in EP No. 40,696 and like compounds, such as those disclosed in U.S. Pat. Nos. 4,283,408; 4,362,736; 4,394,508. The pharmaceutical compositions may also contain a K+/H+ ATPase inhibitor such as omeprazole, disclosed in U.S. Pat. No. 4,255,421, and the like. Each of the references referred to in this paragraph is hereby incorporated herein by reference.

The following examples illustrate the present invention without, however, limiting the same thereto. All temperatures are expressed in degrees Celsius. As used herein, the NMR abbreviations are as follows: s, singlet; d, doublet; t, triplet; q, quartet; qu, quintet; x, sextet; dd, doublet of doublets; and m, multiplet.

The following examples illustrate the present invention without, however, limiting the same thereto. All temperatures are expressed in degrees Celsius.

EXAMPLE 1

Trans,trans-3-(4-acetyl-3-hydroxy-2-propylphenoxy)-2-hydroxy-1-(4-carboxymethylphenylthio)cyclohexane Step A: Preparation of 3-(4-Acetyl-3-hydroxy-2-propylphenoxy)-1-cyclohexene To a mixture of 2,4-dihydroxy-3-propylacetophenone, 40 g, diethyl diazodicarboxylate, 51 g, and cyclohexen-2-ol, 20 g, in tetrahydrofuran, 1.5 L, cooled at 0° C., was added slowly a solution of triphenylphosphine, 80 g, in THF, 0.5 L. The mixture was stirred at room temperature for 18 hours. The volatiles were removed in vacuo. The residue was dissolved in a minimum amount of $CH_2Cl_2$ and placed on a silica gel column. Elution with 1% EtOAc/hexane yielded 20 g of the title compound as an oil. NMR (ppm) ($CDCl_3$): 12.75 (1H, s, phenolic OH), 7.60 (1H, d, J-9 Hz, H ortho to acetyl), 6.53 (1H, d, J-9 Hz, H meta to acetyl), 5.90 (2H, m, olefinic proton), 4.87 (1H, m, CHOAc), 2.60 (3H, s, $CH_3$).

Step B: Preparation of trans 3-(4-Acetyl-3-hydroxy-2-propylphenoxy)-1,2-epoxido-cyclohexane To 3-(4-acetyl-3-hydroxy-2-propylphenoxy)-1-cyclohexene, 11 g, in $CH_2Cl_2$, 800 ml, and in a pH 7 buffer, 800 ml, cooled at 0° C. was added m-chloroperbenzoic acid, 16.6 g. The reaction mixture was allowed to warm to room temperature and was stirred overnight. The 2 phases were decanted, the organic phase was treated with $Ca(OH)_2$, 20 g, and the suspension was stirred 10 minutes. The solids were filtered off and the filtrate was concentrated in vacuo to yield after purification by silica gel chromatography, the title compound, m.p. 68°-71° C.

Step C: Preparation of trans,trans-3-(4-Acetyl-3-hydroxy-2-propylphenoxy)-2-hydroxy-1-(4-carbomethoxymethylphenylthio)cyclohexane A mixture of trans-3-(4-acetyl-3-hydroxy-2-propylphenoxy)-1,2-epoxido-cyclohexane, 0.72 g, 4-mercaptobenzene acetic acid methyl ester, 0.91 g, triethylamine, 0.50 g, in methanol, 25 ml, was refluxed for 2 days. The volatiles were removed in vacuo and the residue was purified by silica gel chromatography to yield the title compound. NMR (ppm) ($CDCl_3$): 12.73 (1H, s, phenolic OH), 7.47 (1H, d, J=9 Hz, H ortho to acetyl), 7.43 (2H, d, J=9 Hz, H ortho to $CH_2$), 7.23 (2H, d, J=9 Hz, H ortho to S), 6.53 (1H, d, J=9 Hz, H meta to acetyl), 4.27 (1H, m, carbinolic H), 3.70 (3H, s, $CH_3O$), 3.63 (2H, s, $CH_2$), 2.53 (3H, s, $CH_3CO$).

Step D: Preparation of trans,trans-3-(4-Acetyl-3-hydroxy-2-propylphenoxy)-2-hydroxy-1-(4-carboxymethylphenylthio)cyclohexane A solution of trans,trans-3-(4-acetyl-3-hydroxy-2-propylphenoxy)-2-hydroxy-1-(4-carbomethoxymethylphenylthio)cyclohexane, 0.65 g, in methanol, 25 ml, and 10N NaOH, 3 ml, was refluxed for 15 minutes. The volatiles were removed in vacuo and the residue, taken up in $H_2O$, 25 ml, was acidified with 20% citric acid and extracted with EtOAc. The extract was washed with water, dried ($Na_2SO_4$) and concentrated in vacuo. The residue crystallized on trituration in hexane to yield the title compound, m.p. 87°-88° C.

Analysis Calc'd: C, 65.42; H, 6.54; S, 6.99; Observed: C, 65.49; H, 6.61; S, 7.31.

EXAMPLE 2

Trans,trans-3-(4-acetyl-3-hydroxy-2-propylphenoxy)-2-hydroxy-1-(4-(3-carboxy-1-oxopropyl)-2-fluorophenylthio)cyclohexane Step A: Preparation of trans,trans-3-(4-acetyl-3-hydroxy-2-propylphenoxy)-2-hydroxy-1-(4-(3-carbomethoxy-1-oxopropyl)-2-fluorophenylthio)cyclohexane Following Step C of Example 1, but substituting 4-mercapto-3-fluorobenzene-4-oxobutanoic acid methyl ester for 4-mercapto benzene acetic acid methyl ester, the title compound was prepared. NMR (ppm) ($CDCl_3$): 12.77 (1H, s, phenolic OH), 7.53 (1H, d, J=9 Hz, H ortho to acetyl), 6.53 (1H, d, J=9 Hz, H meta to acetyl), 4.30 (1H, m, carbinolic H), 3.70 (3H, s, $CH_3O$), 2.53 (3H, s, $CH_3CO$).

Step B: Preparation of Trans,trans-3-(4-acetyl-3-hydroxy-2-propylphenoxy)-2-hydroxy-1-(4-(3-carboxy-1-oxopropyl)-2-fluorophenylthio)cyclohexane Following Step D of Example 1, but substituting the title compound of Step A of this Example for the title compound of Step C of Example 1, the title compound, m.p. 100°-103° C., was prepared.

Analysis Calc'd: C, 62.53; H, 6.02; F, 3.66; S, 6.18; Observed: C, 62.50; H, 3.95; F, 3.40; S, 6.24.

EXAMPLE 3

Trans,trans-3-(4-acetyl-3-hydroxy-2-propylphenoxy)-2-hydroxy-1-(4-(3-carboxy-1-oxopropyl)-2-fluorophenylthio)cyclohexane-S-oxide Step A: Preparation of trans,trans-3-(4-acetyl-3-hydroxy-2-propylphenoxy)-2-hydroxy-1-(4-(3-carbomethoxy-1-oxopropyl)-2-fluorophenylthio)cyclohexane-S-oxide The product obtained in Step A of Example 2, 1.0 g, in $CH_2Cl_2$, 30 ml, was treated with m-chloro perbenzoic acid, 400 mg, for 120 minutes at 0° C. $Ca(OH)_2$, 3 g, was added and the resulting suspension was stirred for 10 minutes. The solids were filtered off and the filtrate was concentrated to a small volume in vacuo which was placed on a silica gel column. Elution with 40% EtOAc/hexane gave 400 mg of a major isomer of the title compound, and 200 mg of a minor isomer of the title compound.

Major isomer: NMR (ppm) ($CDCl_3$): 12.70 (1H, s, phenolic OH), 7.50 (1H, d, J=9 Hz, H ortho to acetyl), 6.50 (1H, d, J=9 Hz, H meta to acetyl), 3.67 (3H, s, $CH_3O$), 2.50 (3H, s, $CH_3CO$).

Minor isomer: NMR (ppm) ($CDCl_3$): 12.70 (1H, s, phenolic OH), 7.50 (1H, d, J=9 Hz, H ortho to acetyl), 6.50 (1H, d, J=9 Hz, H meta to acetyl), 3.67 (3H, s, $CH_3O$), 2.50 (3H, s, $CH_3CO$).

Step B: Preparation of trans,trans-3-(4-acetyl-3-hydroxy-2-propylphenoxy)-2-hydroxy-1-(4-(3-carboxy- 1-oxopropyl)-2-fluorophenylthio)cyclohexane-S-oxide, major isomer Following Step D of Example 1, but substituting the title compound of Step A of this example for the title compound of Step C of Example 1, the major isomer of the title compound, m.p. 90°–95° C., was obtained.

Analysis Calc'd: C, 60.66; H, 5.84; F, 3.55; S, 5.99; Observed: C, 60.63; H, 5.89; F, 3.34; S, 6.10.

Step C: Preparation of trans,trans-3-(4-acetyl-3-hydroxy-2-propylphenoxy)-2-hydroxy-1-(4-(3-carboxy-1-oxopropyl)-2-fluorophenylthio)cyclohexane-S-oxide, minor isomer Following Step D of Example 1, but substituting the title compound of Step A of this Example for the title compound of Step C of Example 1, the minor isomer of the title compound, m.p. 90°–92° C., was obtained.

Analysis Calc'd: C, 60.66; H, 5.84; F, 3.55; S, 5.99; Observed: C, 60.71; H, 5.98; F, 3.29; S, 5.97.

EXAMPLE 4

Trans,trans-3-(4-acetyl-3-hydroxy-2-propylphenoxy)-2-hydroxy-1-(4-(3-carboxy-1-oxopropyl)phenylthio)cyclohexane Step A: Preparation of trans,trans-3-(4-acetyl-3-hydroxy-2-propylphenoxy)-2-hydroxy-1-(4-(3-carboxy-1-oxopropylphenylthio)cyclohexane methyl ester Following Step C of Example 1, but substituting 4-mercaptobenzene-4-oxobutanoic acid methyl ester for 4-mercapto benzene acetic acid methyl ester the title compound was obtained as an oil.

NMR (ppm) (CDCl$_3$): 12.75 (1H, s, phenolic OH), 7.57 (1H, d, J=9 Hz, H ortho to acetyl), 6.53 (1H, d, J=9 Hz, meta to acetyl), 3.70 (3H, s, CH$_3$O), 2.53 (3H, s, CH$_3$CO).

Step B: Preparation of trans,trans-3-(4-acetyl-3-hydroxy-2-propylphenoxy)-2-hydroxy-1-(4-(3-carboxy-1-oxopropylphenylthio)cyclohexane sesquihydrate Following Step D of Example 1, but substituting the title compound of Step A of this Example for the title compound of Step C of Example 1, the title compound, m.p. 72°–75° C., was obtained.

Analysis calc'd: C, 61.46; H, 6.68; S, 6.08; Obtained: C, 61.39; H, 6.25; S, 6.98.

EXAMPLE 5

Trans,trans-3-(4-acetyl-3-hydroxy-2-propylphenoxy)-2-hydroxy-1-(4-carboxymethylphenoxy)cyclohexane Step A: Preparation of Trans,trans-3-(4-acetyl-3-hydroxy-2-propylphenoxy)-2-hydroxy-1-(4-carboxymethylphenoxy)cyclohexane methyl ester A mixture of 2,3-epoxido-1-(4-acetyl-3-hydroxy-2-propylphenoxy)cyclohexane, from Example 1, Step B (1.3 g) and p-hydroxybenzeneacetic acid, methyl ester (4.0 g) were heated under N$_2$ for 4 hours in an oil bath at 200° C. The reaction mixture was cooled, dissolved in CH$_2$Cl$_2$. Excess p-hydroxybenzeneacetic acid methyl ester, was removed by washing the CH$_2$Cl$_2$ layer with 1N NaOH. The organic layer was washed with H$_2$O, dried (Na$_2$SO$_4$) and evaporated to dryness. The residue was chromatographed on silica gel to yield 0.5 g of title compound as an oil.

NMR (ppm) (CDCl$_3$): 12.77 (1H, s, phenolic OH), 7.63 (1H, d, J=9 Hz, H ortho to acetyl), 6.63 (1H, d, J=9 Hz, H meta to acetyl), 4.27 (1H, m, carbinolic proton), 3.73 (3H, s, CH$_3$O), 2.53 (3H, s, CH$_3$CO).

Step B: Preparation of trans,trans-3-(4-acetyl-3-hydroxy-2-propylphenoxy)-2-hydroxy-1-(4-carboxymethylphenoxy)cyclohexane Following Step D of Example 1, but substituting the title compound of Step A of this Example for the title compound of Step C of Example 1, the title compound, m.p. 96°–98° C., was obtained.

Analysis Calc'd: C, 67.87; H, 6.78; Obtained: C, 67.70; H, 6.92.

EXAMPLE 6

Cis-3-(4-acetyl-3-hydroxy-2-propylphenoxy)-1-(4-(3-carboxy-1-oxopropyl)phenylthio)cyclohexane Step A: Preparation of 3-4-(3-carbomethoxy-1-oxopropylphenylthio)cyclohexanone 3-Cyclohexen-one (0.86 g), 4-mercaptobenzene-4-oxobutanoic acid methyl ester (2 g), and triethylamine (0.9 g) in toluene (100 ml) were stirred at room temperature for 4 hours. The volatiles were removed in vacuo and the residue was chromatographed on silica gel to yield 2.8 g of the title compound as an oil.

NMR: (ppm) (CDCl$_3$) Hz, H ortho to C=O), 7.37 (2H, d, J=9 Hz, H meta to C=O), 3.67 (3H, s, CH$_3$O), 3.27 (2H, t, J=7 Hz, CH$_2$ alpha to COOMe), 2.73 (2H, t, J-7 Hz, CH$_2$ beta to COOMe), 2.40–1.70 (8H, m, cyclohexane protons).

Step B: Preparation of trans-3-(3-carbomethoxy-1-oxopropyl)phenylthio)-1-cyclohexanol The title compound of Step A of this Example was dissolved in THF (100 ml) and to the resulting solution cooled at −78° C., was added 8.7 ml of 1M L-selectride dropwise. The reaction mixture was stirred for 1 hour. It was then quenched with water and was extracted with EtOAc. The extracts were washed with brine, dried (Na$_2$SO$_4$) and evaporated to dryness. The residue was chromatographed on silica gel. Elution with 25% EtOAc/toluene yielded 0.76 g of the title compound as an oil.

NMR (ppm) (CDCl$_3$): 7.90 (2H, d, J=9 Hz, H ortho to C=O), 7.40 (2H, d, J=9 Hz, H meta to C=O), 4.50 (1H, m, carbinolic proton), 3.70 (3H, s, CH$_3$O), 3.30 (2H, t, J-7 Hz, CH$_2$ alpha to COOMe), 2.77 (2H, t, J-7 Hz, CH$_2$, beta to COOMe), 2.0–1.5 (8H, m, cyclohexane protons).

Further elution gave 0.4 g of the cis-isomer of the title compound as an oil.

NMR (ppm) (CDCl$_3$): carbinolic proton at 3.50 as a multiplet.

Step C: Preparation of trans-3-(4-(3-carbomethoxy-1-oxopropyl)phenylthio)-1-mesyloxy-cyclohexane This title compound of Step B of this Example (0.76 g) dissolved in pyridine (20 ml) was reacted with methanesulfonyl chloride (0.3 g). The resulting mixture was stirred at room temperature overnight. The volatiles were removed in vacuo and the residue, taken up in 10% citric acid, was extracted with EtOAc. The extracts were washed with brine, dried (Na$_2$SO$_4$) and concentrated in vacuo to yield 0.93 g of the title compound.

NMR (ppm) (CDCl$_3$): 5.10 (1H, m, carbinolic proton), 3.03 (3H, s, CH$_3$SO$_2$—).

Similarly, the cis-isomer of this step was obtained from the reaction of the cis-alcohol obtained in Step B of this example, with methanesulfonyl chloride in pyridine. The compound was characterized by NMR adsorption of the carbinolic proton at 4.67 ppm as a multiplet and by the adsorption of the methanesulfonyl group at 3.00 ppm as a singlet.

Step D: Preparation of cis-3-(4-acetyl-3-hydroxy-2-propylphenoxy)-1-(4-(3-carbomethoxy-1-oxopropyl)-phenylthio)cyclohexane methyl ester The title compound of Step C of this Example (1 g) was reacted with 2,4-dihydroxy-3-propyl acetophenone (0.54 g) using sodium hydride as the base in toluene (40 ml) at reflux for 5 hours. The reaction mixture was poured on ice and was extracted with chloroform. The organic phase was washed with brine, dried ($Na_2SO_4$) and concentrated to yield a residue that was chromatographed on silica gel. Elution with 20% ethyl acetae in hexane gave the title compound as an oil.

NMR (ppm) ($CDCl_3$): 12.77 (1H, s, phenolic OH), 7.92 (2H, d, J=9 Hz, H alpha to CO), 7.60 (1H, d, J=9 Hz, H alpha to acetyl), 7.43 (2H, d, J=9 Hz, H beta to CO), 6.50 (1H, d, J=9 Hz, H beta to acetyl), 3.70 (3H, s, $CH_3O$), 2.53 (3H, s, $CH_3CO$).

Similarly, the trans-isomer of this step was obtained from the reaction of the cis-mesylate. NMR (ppm) ($CDCl_3$): 4.80 (broad s, 1H, carbinolic proton), 3.73 (3H, S, $OCH_3$), 2.60 (3H, S, $CH_3CO$).

Step E: Preparation of cis-3-(4-acetyl-3-hydroxy-2-propylphenoxy)-1-(4-(3-carboxy-1-oxopropyl)phenylthio)cyclohexane Following Step D of Example 1, but substituting the title compound of Step D of this Example for the title compound of Step C of Example 1, the title compound, m.p. 101°–103° C., was obtained.

Similarly, the trans-isomeric methyl ester is hydrolyzed to the trans-isomer of the title compound.

EXAMPLE 7

Trans-3-(4-acetyl-3-hydroxy-2-propylphenoxy)-1-(4-carboxymethylphenylthio)cyclohexane Step A: Preparation of 3-(4-carbomethoxymethylphenylthio)cyclohexanone Following Step A of Example 6 but substituting 4-mercapto benzene acetic acid methyl ester for 4-mercapto benzene-4-oxo butanoic acid methyl ester, the title compound was obtained as an oil.

NMR (ppm) ($CDCl_3$): 7.40 (2H, d, J=9 Hz, H meta to s), 7.23 (2H, d, J=9 Hz, H ortho to S), 3.67 (3H, s, $CH_3O$), 3.57 (2H, s, $CH_2$), 2.60–1.50 (8H, m, cyclohexane protons).

Step B: Preparation of cis-3-(4-carbomethoxymethylphenylthio)cyclohexanol

Following Step B of Example 6 but substituting the title compound of Step A of this Example for 3-(4-(3-carbomethoxy-1-oxopropyl)phenylthio)cyclohexanone, the title compound was obtained as an oil. NMR (ppm) ($CDCl_3$): 7.33 (2H, d, J=9 Hz, H meta to S), 7.17 (2H, d, J=9 Hz, H ortho to S), 4.00 (1H, m, carbinolic proton). 3.60 (3H, s, $CH_3O$), 3.50 (2H, s, $CH_2$), 1.90–1.30 (8H, m, cyclohexane protons).

The trans-isomer was also isolated as an oil. NMR (ppm) ($CDCl_3$): 3.50 (1H, m, carbinolic proton).

Step C: Preparation of trans-3-(4-carbomethoxyphenylthio)-1-mesyloxy cyclohexane Following Step C of Example 6, but substituting the title compound of Step B of this Example for trans-3-(4-carbomethoxy-1-oxopropyl)phenylthio)cyclohexanol, the title compound was obtained as an oil.

NMR (ppm) ($CDCl_3$): 5.07 (m, 1H, carbinolic proton), 2.97 (3H, s, $CH_3SO_2$).

Similarly, the cis-isomer is obtained from the reaction of the cis-isomer, prepared in Step B of this Example, with methanesulfonyl chloride.

Step D: Preparation of cis-3-(4-acetyl-3-hydroxy-2-propylphenoxy)-1-(4-carboxymethylphenylthio)cyclohexane methyl ester Following Step D of Example 7, but substituting the title compound of Step C of this Example for the title compound of Step C of Example 6, the title compound was obtained as an oil.

NMR (ppm) ($CDCl_3$): 12.80 (1H, s, phenolic OH), 7.50 (1H, d, J=9 Hz, H ortho to acetyl), 7.40 (2H, d, J=9 Hz, H meta to S), 7.17 (2H, d, J=9 Hz, H ortho to S), 6.27 (1H, d, J=9 Hz, H meta to acetyl), 4.10 (1H, m, carbinolic H), 3.63 (3H, s, $CH_3O$), 3.53 (2H, s, $CH_2$), 2.43 (3H, s, $CH_3CO$).

Similarly, reaction of the cis-isomer gives the trans-isomer of the title compound.

Step E: Preparation of cis,-3-(4-acetyl-3-hydroxy-2-propylphenoxy)-1-(4-carboxymethylphenylthio)cyclohexane Following Step E of Example 7, but substituting the title compound of Step D of this Example for the title compound of Step D of Example 7, the title compound was obtained as an oil.

Elemental Analysis Calc'd: C, 67.84; H, 6.83; S, 7.24; Obtained: C, 67.82; H, 6.91; S, 7.43.

Similarly, the trans-isomeric methyl ester is hydrolyzed to the trans-isomer of the title compound.

EXAMPLE 8

Trans-3-(4-acetyl-3-hydroxy-2-propylphenoxy)-1-(4-carboxymethyl-2-bromo phenoxy)cyclohexane Step A: Preparation of cis- and trans-3-mesyloxycyclohexanol To a solution of cyclohexanediol (58 g; 0.5 mole) in methylene chloride (2.5 l) stirred at −5° C. was added triethylamine (100 ml), followed by the dropwise addition of methanesulfonyl chloride (58 g; 0.5 mole). The mixture was stirred at room temperature for 16 hours. It was then poured into water. The organic phase was decanted, washed successfully with 5% sodium bicarbonate and brine, dried ($Na_2SO_4$) and concentrated in vacuo. Chromatography on silica gel afforded 52 g of the cis and trans isomers of the title compound and 17 g of the cis- and trans-1,3-dimesyloxycyclohexane. The cis-trans mixture was used as obtained in the subsequent reactions.

Step B: Preparation of cis- and trans-3-(4-acetyl-3-hydroxy-2-propylphenoxy)-cyclohexanol To a cis-trans mixture of the title compound of Step A of Example 8 (2.24 g; 11.5 mmoles) in toluene (45 ml) was added 3-propyl-2,4-dihyroxyacetophenone (1.99 g; 10 mmoles, sodium hydride (240 mg; 10 mmole) was then added, followed by 15-crown-5 (50 mg). The mixture was refluxed for 6 hours under nitrogen. The mixture was poured in 5% citric acid and extracted with ethyl acetate. The organic layer was dried and evaporated in vacuo. The residue was chromatographed on silica gel to yield successively 800 mg of the cis-isomer of the title compound and 1.46 g of the trans-isomer of the title compound.

cis-isomer: NMR (ppm) ($CDCl_3$), 7.57 (1H, d, J=9 Hz, H ortho to acetyl), 6.47 (1H, d, J=9 Hz, H meta to acetyl), 4.80 (1H, broad s, axial $H_3$), 3.92 (1H, broad s, axial H,), 2.50 (3H, s, acetyl).

trans isomer: NMR (ppm) (CDCl$_3$) 7.59 (1H, d, J=9 Hz, H ortho to acetyl), 6.48 (1H, a, J=9 Hz, H meta to acetyl) 4.6 (1H, broad, axial H$_3$) 3.70 (1H, broad, equatorial H$_3$)

Step C: Preparation of cis-3-(4-acetyl-3-hydroxy-2-propylphenoxy)-1-mesyloxycyclohexane By following the procedure of Step A of this example and substituting the cis-isomer of the title compound of Step B of this example for cyclohexane diol, the title compound of this step was obtained as an oil.

NMR (ppm) (CDCl$_3$) 7.60 (1H, d, J=9 Hz, H ortho to acetyl), 6.43 (1H, d, J=9 Hz, H meta to acetyl), 4.80 (1H, m, H$_3$), 4.38 (1H, m, H1), 3.00 (3H, s, CH$_3$SO$_2$), 2.57 (3H, s, CH$_3$CO).

Step D: Preparation of trans-3-(4-acetyl)-3-hydroxy-2-propylphenoxy)-1-mesyloxycyclohexane By following the procedure of Step A of this example and substituting the trans-isomer of the title compound of Step B of this example for cyclohexane diol, the title compound of this step was obtained as an oil.

NMR (ppm) (CDCl$_3$) 7.58 (1H, d, J=9 Hz, H ortho to acetyl), 6.40 (1H, d, J=9 Hz, H meta to acetyl), 4.70 (1H, m, H$_3$), 4.33 (1H, m, H,), 2.97 (3H, s, CH$_3$SO$_2$), 2.50 (3H, s, CH$_3$CO).

Step E: Preparation of trans-3-(4-acetyl-3-hydroxy-2-propylphenoxy)-1-(4-carbomethoxymethyl-2-bromophenoxy)cyclohexane To a solution of the title compound of Step C of this example (500 mg; 1.35 mmole) in toluene (30 ml) and THF (1.5 ml) was added successively 4-hydroxy-3-bromophenylacetic acid, methyl ester (1 g, 4 mmoles), sodium hydride (169 mg; 7 mmoles) and 15-crown-5 (10 mg). The reaction mixture was refluxed for 10 hours under nitrogen. It was then worked-up as in Step B of Example 8 to yield the title compound of this step.

Step F: Preparation of trans-3-(4-acetyl-3-hydroxy-2-propylphenoxy)-1-(4-carboxymethyl-2-bromo phenoxy)cyclohexane Following Step D of Example 1, but substituting the title compound of Step E of this example for the title compound of Step C of Example 1, the title compound was obtained.

NMR (ppm) (CDCl$_3$) 7.50 (1H, d, 5=9 Hz, H ortho to acetyl), 6.37 (1H, d, 5=9 Hz, H meta to acetyl), 6.80 (1H, d, J=9 Hz, H meta to Bu), 7.10 (1H, d, J=2 Hz, H para to Br), 3.50 (2H, s, CH$_2$), 2.50 (3H, s, CH$_3$CO).

EXAMPLE 9

Cis-3-(4-acetyl-3-hydroxy-2-propylphenoxy)-1-(4-carboxymethyl-2-bromophenoxy)cyclohexane Step A: Preparation of cis-3-(4-acetyl-3-hydroxy-2-propyl-phenoxy)-1-(4-carbomethoxy methyl-2-bromo phenoxy)cyclohexane By following Step E of Example 8, but substituting the title compound of Step D of Example 8 for the title compound of Step C of Example 8, the title compound of this step was obtained as an oil.

NMR (ppm) (CDCl$_3$), 7.57 (1H, d, J=9 Hz, H ortho to acetyl), 6.43 (1H, d, J=9 Hz, H meta to acetyl), 6.90 (1H, d, J=9 Hz, H meta to Bu), 7.20 (1H, d of d, J=2 Hz, 9 Hz, H para to Bu), 4.30 (2H, m, H, and H$_3$), 3.67 (3H, s, CH$_3$O) 3.50 (2H, s, CH$_2$), 2.50 (3H, s, CH$_3$CO).

Step B: Preparation of cis-3-(4-acetyl-3-hydroxy-2-propylphenoxy)-1-(4-carboxymethyl-2-bromophenoxy)cyclohexane Following Step D of Example 1, but substituting the title compound of Step A of this example for the title compound of Step C of Example 1, the title compound was obtained.

NMR (ppm) (CDCl$_3$) 7.55 (1H, d, J=9 Hz, H ortho to acetyl), 6.47 (1H, d, J=9 Hz, H meta to acetyl), 6.88 (1H, d, J=9 Hz, H meta to Br), 7.22 (1H, d of d, J=2 Hz, 9 Hz, H para to Br), 4.30 (2H, m, H and H$_3$), 3.50 (2H, s, CH$_2$), 3.66 (3H, s, CH$_3$CO).

EXAMPLE 10

Trans-3-(4-acetyl-3-hydroxy-2-propylphenoxy)-1-(4-(3-carboxy-1-oxopropyl)phenoxy)cyclohexane Step A: Preparation of trans 3-(4-acetyl-3-hydroxy-2-propyl-phenoxy)-1-(4-(3-carbomethoxy-1-oxo propyl)-phenoxy)-cyclohexane By following Step E of Example 8, but substituting 4-(4-hydroxyphenyl)-4-oxobutyric acid methyl ester for 4-hydroxy-3-bromophenylacetic acid methyl ester, the title compound of this step was obtained as an oil.

NMR (ppm) (CDCl$_3$) 7.97 (2H, d, J=9 Hz, H ortho to CO), 7.57 (1H, d, J=9 Hz, H ortho to acetyl), 6.93 (2H, d, J=9 Hz, H meta to COO), 6.40 (1H, d, J=9 Hz, H meta to acetyl), 4.83 (2H, m, H$_1$ and H$_3$), 3.70 (3H, s, CH$_3$O) 2.57 (3H, s, CH$_3$CO).

Step B: Preparation of trans-3-(4-acetyl-3-hydroxy-2-propyl phenoxy)-1-(4-(3-carboxy-1-oxopropyl)phenoxy)-cyclohexane By following Step D of Example 1, but substituting the title compound of Step A of this Example for the title compound of Step C of Example 1, the title compound of this example was obtained as a solid, m.p. 90°-94°.

NMR (ppm) (CDCl$_3$) 8.00 (2H, d, J=9 Hz, H ortho to C=O), 7.62 (1H, d, J=9 Hz, H ortho to acetyl), 6.97 (2H, d, J=9 Hz, H meta to C=O), 6.42 (1H, d, J=9 Hz, H meta to acetyl), 4.80 (2H, m, H$_1$ and H$_3$), 2.42 (3H, s, CH$_3$CO).

EXAMPLE 11

Cis-3-(4-acetyl-3-hydroxy-2-propylphenoxy)-1-(4-(3-carboxy-1-oxo-propylphenoxy)cyclohexane Step A: Preparation of cis-3-(4-acetyl-3-hydroxy-2-propylphenoxy)-1-(4-(3-carbomethoxy-1-oxopropylphenoxy)-cyclohexane By following Step A of Example 10, but substituting the title compound of Step D of Example 8 for title compound of Step C of Example 8, the title compound of this step was obtained as an oil.

NMR (ppm) (CDCl$_3$) 7.93 (2H, d, J=9 Hz, H ortho to C=O), 7.65 (1H, d, J=9 Hz, H ortho to acetyl), 6.90 (2H, d, J=9 Hz, H meta to C=O), 6.40 (1H, d, J=9 Hz, H meta to acetyl), 4.30 (2H, m, H$_3$ and H$_1$), 3.67 (3H, s, CH$_3$O), 2.45 (3H, s, CH$_3$CO).

Step B: Preparation of cis-3-(4-acetyl-3-hydroxy-2-propylphenoxy)-1-(4-(3-carboxy-1-oxo-propyl)phenoxy)-cyclohexane By following Step D of Example 1, but substituting the title compound of Step A of this example for the title compound of Step C of Example 1, the title compound of this example was obtained as an oil.

NMR (ppm) (CDCl$_3$) 7.90 (2H, d, J=9 Hz, H ortho to C=O), 7.50 (1H, d, J=9 Hz, H ortho to acetyl), 7.86 (2H, d, J=9 Hz, H meta to C=O), 6.40 (1H, d, J=9 Hz, H meta to acetyl), 4.87 (2H, m, H$_3$ and H$_1$), 2.53 (3H, s, CH$_3$CO).

EXAMPLE 12

Trans-3-(4-acetyl-3hydroxy-2-propylphenoxy)-1-(4-carboxymethylphenoxy)-cyclohexane Step A: Preparation trans-3-(4-acetyl-3-hydroxy-2-propylphenoxy)-1-(4-carbomethoxymethylphenoxy)-cyclohexane By following Step E of Example 8, but substituting 4-hydroxyphenylacetic acid, methyl ester for 4-hydroxy-3-bromophenylacetic acid, methyl ester, the title compound of this step was obtained as an oil.

NMR (ppm) (CDCl$_3$) 7.63 (1H, d, J=9 Hz, H ortho to acetyl), 7.27 (2H, d, J=9 Hz, H ortho to CH$_2$), 6.93 (2H, d, J=9 Hz, H meta to CH$_2$), 6.43 (1H, d, J=9 Hz, H, meta to acetyl), 4.80 (2H, m, H$_3$ and H$_1$), 3.70 (3H, s, CH$_3$O), 3.57 (2H, s, CH$_2$), 2.57 (3H, s, CH$_3$CO).

Step B: Preparation of trans-3-(4-acetyl-3-hydroxy-2-propylphenoxy)-1-(4-carboxymethylphenoxy)cyclohexane By following Step D of Example 1, but substituting the title compound of Step A of this example for the title compound of Step C of Example 1, the title compound of this example was obtained as an oil.

NMR (ppm) (CDCl$_3$), 7.60 (1H, d, J=9 Hz, H ortho to acetyl), 7.21 (2H, d, J=9 Hz, H ortho to CH$_2$), 6.88 (2H, d, J=9 Hz, H meta to CH$_2$), 6.39 (1H, d, J=9 Hz, H meta to acetyl), 4.80 (2H, m H$_3$ and H$_1$), 3.56 (2H, s, CH$_2$), 3.67 (3H, s, CH$_3$CO).

EXAMPLE 13

Cis-3-(4-acetyl-3-hydroxy-2-propylphenoxy)-1-(4-carboxymethylphenoxy)-cyclohexane Step A: Preparation of cis-3-(4-acetyl-3-hydroxy-2-propyl phenoxy)-1-(4-carbomethoxymethylphenoxy)-cyclohexane By following Step A of Example 10, but substituting para-hydroxybenzeneacetic acid methyl ester for 4-(4-hydroxyphenyl)-4-oxobutyric acid methyl ester and substituting the title compound of Step D of Example 8 for the title compound of Step C of Example 8, the title compound of this step was obtained as an oil.

NMR (ppm) (CDCl$_3$), 7.57 (1H, d, J=9 Hz, H ortho to acetyl), 7.20 (2H, d, J=9 Hz, H ortho to CH$_2$), 6.83 (2H, d, J=9 Hz, H meta to CH$_2$), 6.43 (1H, d, J=9 Hz, H meta to acetyl), 4.30 (2H, m, H$_3$ and H), 3.67 (3H, s, CH$_3$O), 3.53 (2H, s, CH$_2$), 2.53 (3H, s, CH$_3$CO).

Step B: Preparation of cis-3-(4-acetyl-3-hydroxy-2-propylphenoxy)-1-(4-carboxymethylphenoxy)-cyclohexane By following Step D of Example 1, but substituting the title compound of Step A of this example for the title compound of Step C of Example 1, the title compound of this example was obtained as an oil.

NMR (ppm) (CDCl$_3$), 7.53 (1H, d, J=9 Hz, H ortho to acetyl), 7.20 (2H, d, J=9 Hz, H ortho to CH$_2$), 6.84 (2H, d, J=9 Hz, H meta to CH$_2$), 6.44 (1H, d, J=9 Hz, H meta to acetyl), 4.26 (2H, m, H$_3$ and H$_1$), 3.52 (2H, s, CH$_2$), 3.68 (3H, s, CH$_3$CO).

Claims to the invention follow.
What is claimed is:

1. A compound having the formula Ia:

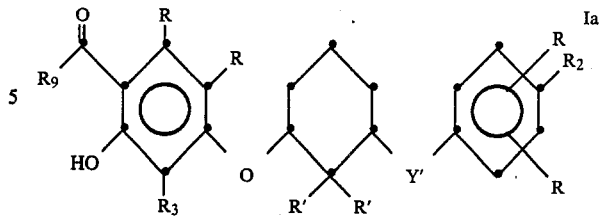

wherein
each R is independently H, alkyl of 1 to 6 carbon atoms which may be straight chain or branched; trifluoromethyl; halogen; or $N(R_4)_2$;
each R' is independently $R_4$ or $OR_4$;
Y' is oxygen, sulfur, sulfoxide or sulfone;
$R_2$ is

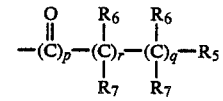

wherein:
each $R_4$ is independently H or alkyl of 1 to 6 carbon atoms which may be straight chain or branched;
each $R_6$ is independently H or alkyl of 1 to 4 carbons;
each $R_7$ is independently H, OH, or alkyl of 1 to 4 carbons;
$R_5$ is $COOR_4$;
r and q are each independently 0 to 3; and
p is 0 or 1;
$R_3$ is alkyl of 1 to 6 carbon atoms which may be straight chain or branched; or alkenyl of 3 to 6 carbon atoms which may be straight chain or branched;
$R_9$ is alkyl of 1 to 6 carbon atoms which may be straight chain or branched; or a pharmaceutically acceptable salt or acid addition salt thereof.

2. The compounds of claim 1:
trans,trans-3-(4-acetyl-3-hydroxy-2-propylphenoxy)-2-hydroxy-1-(4-carboxymethylphenylthio)cyclohexane;
trans,trans-3-(4-acetyl-3-hydroxy-2-propylphenoxy)-2-hydroxy-1-(4-(3-carboxy-1-oxopropyl)-2-fluorophenylthio)cyclohexane;
trans,trans-1-(4-acetyl-3-hydroxy-2-propylphenoxy)-2-hydroxy-1-(4-(3-carboxy-1-oxopropyl)-2-fluorophenylthio)cyclohexane-S-oxide;
trans,trans-3-(4-acetyl-3-hydroxy-2-propylphenoxy)-2-hydroxy-1-(4-(3-carboxy-1-oxopropyl)phenylthio)-cyclohexane;
trans,trans-3-(4-acetyl-3-hydroxy-2-propylphenoxy)-2-hydroxy-1-(4-carboxymethylphenoxy)cyclohexane;
cis-3-(4-acetyl-3-hydroxy-2-propylphenoxy)-1-(4-(3-carboxy-1-oxopropyl)phenylthio)cyclohexane; and
trans-3-(4-acetyl-3-hydroxy-2-propylphenoxy)-1-(4-carboxymethylphenylthio)cyclohexane;
trans-3-(4-acetyl-3-hydroxy-2-propylphenoxy)-1-(4-carboxymethyl-2-bromo phenoxy)cyclohexane;
cis-3-(4-acetyl-3-hydroxy-2-propylphenoxy)-1-(4-carboxymethyl-2-bromophenoxy)cyclohexane;
trans-3-(4-acetyl)-3-hydroxy-2-propylphenoxy)-1-(4-(3-carboxy-1-oxopropyl)phenoxy)cyclohexane;
cis-3-(4-acetyl-3-hydroxy-2-propylphenoxy)-1-(4-(3-carboxy-1-oxo-propyl)phenoxy)cyclohexane;
trans-3-(4-acetyl-3-hydroxy-2-propylphenoxy)-1-(4-carboxymethylphenoxy)-cyclohexane;
cis-3-(4-acetyl-3-hydroxy-2-propylphenoxy)-1-(4-carboxymethylphenoxy)-cyclohexane.

3. A composition for antagonizing leukotriene action in a mammal comprising an effective amount of a compound of claim 1 and a pharmaceutically acceptable carrier.

4. A method of antagonizing leukotriene action in a mammal which comprises administering to a mammal an amount of a compound of claim 1 effective as a leukotriene antagonist.

* * * * *